(12) United States Patent
Bruder et al.

(10) Patent No.: US 7,127,025 B2
(45) Date of Patent: Oct. 24, 2006

(54) METHOD FOR PRODUCTION OF TOMOGRAPHIC SECTION IMAGES OF A PERIODICALLY MOVING OBJECT WITH A NUMBER OF FOCUS DETECTOR COMBINATIONS

(75) Inventors: Herbert Bruder, Hoechstadt (DE); Thomas Flohr, Uehlfeld (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/995,339

(22) Filed: Nov. 24, 2004

(65) Prior Publication Data

US 2005/0111623 A1    May 26, 2005

(30) Foreign Application Priority Data

Nov. 24, 2003    (DE) ................. 103 54 900

(51) Int. Cl.
*A61B 6/03* (2006.01)
*G01N 23/00* (2006.01)

(52) U.S. Cl. ................. 378/8; 378/95; 378/9
(58) Field of Classification Search ........... 378/9, 378/8, 95
See application file for complete search history.

(56) References Cited

U.S. PATENT DOCUMENTS

| | | | |
|---|---|---|---|
| 4,196,352 A | 4/1980 | Berninger et al. | |
| 4,384,359 A | 5/1983 | Franke | |
| 4,991,190 A | 2/1991 | Mori | |
| 5,654,820 A * | 8/1997 | Lu et al. ............. | 359/298 |
| 5,966,422 A | 10/1999 | Dafni et al. | |
| 6,041,097 A | 3/2000 | Roos et al. | |
| 6,233,478 B1 * | 5/2001 | Liu ..................... | 600/428 |
| 6,421,412 B1 | 7/2002 | Hsieh et al. | |
| 6,445,761 B1 | 9/2002 | Miyazaki et al. | |
| 6,504,893 B1 | 1/2003 | Flohr et al. | |
| 6,556,697 B1 | 4/2003 | Bruder et al. | |
| 6,865,248 B1 * | 3/2005 | Rasche et al. ........ | 378/8 |
| 6,873,677 B1 * | 3/2005 | Kaufman ............. | 378/4 |
| 2003/0133533 A1 | 7/2003 | Bruder et al. | |
| 2004/0114708 A1 | 6/2004 | Bruder et al. | |

FOREIGN PATENT DOCUMENTS

DE    198 42 238 A1    4/2000

(Continued)

OTHER PUBLICATIONS

Thomas Flohr et al., "Heart Rate Adaptive Optimization of Spatial and Temporal Resolution for Electrocardiogram-Gated Multislice Spiral CT of the Heart", Journal of Computer Assisted Tomography, vol. 25, No. 6, 2001, pp. 907-923.

(Continued)

*Primary Examiner*—Edward J. Glick
*Assistant Examiner*—Krystyna Suchecki
(74) *Attorney, Agent, or Firm*—Harness, Dickey & Pierce

(57) ABSTRACT

A method is for production of tomographic section images, in particular X-ray CT images, of an at least partially periodically moving examination object with periodically changing movement and rest phases, preferably of a heart of a living being. A number of focus detector combinations are used, with the time resolution of the CT scanner being significantly increased by supplementary combination of detector data in the correct phase. On the one hand, a number of focus detector combinations which scan an examination object at the same time are used; and on the other hand a number of adjacent movement cycles of a periodically moving examination object are performed.

31 Claims, 4 Drawing Sheets

FOREIGN PATENT DOCUMENTS

| | | |
|---|---|---|
| DE | 199 57 082 A1 | 8/2001 |
| DE | 101 59 927 A1 | 6/2003 |
| DE | 102 07 623 A1 | 11/2003 |
| DE | 102 44 180 A1 | 4/2004 |
| DE | 103 02 565 A1 | 8/2004 |

OTHER PUBLICATIONS

H. Bruder et al., "A Novel Reconstruction Scheme for Cardiac Volume Imaging with MSCT Providing Cone Crrection", Medical Imaging 2002, vol. 4684, pp. 65-73.

H. Turbell, "An Improved PI-method for reconstruction from helical cone-beam projections", IEEE 2000, pp. 865-868.

* cited by examiner

METHOD FOR PRODUCTION OF TOMOGRAPHIC SECTION IMAGES OF A PERIODICALLY MOVING OBJECT WITH A NUMBER OF FOCUS DETECTOR COMBINATIONS

The present application hereby claims priority under 35 U.S.C. §119 on German patent application number DE 103 54 900.5 filed Nov. 24, 2003, the entire contents of which are hereby incorporated herein by reference.

FIELD OF THE INVENTION

The invention generally relates to a method for production of tomographic section images. In particular, it relates to a method for production of X-ray CT images, of a periodically moving object with periodically changing movement and rest phases, with a number of focus detector combinations being moved on coaxially running paths around the examination object in order to scan the periodically moving examination object, and movement signals from the examination object at the same time being measured in order to determine movement and rest phases, and being stored correlated with the detector output signals. Tomography images can then be created with the aid of back-projections by spiral reconstruction and reformatting, on the basis of the stored detector output signals.

BACKGROUND OF THE INVENTION

Computer tomography methods for creation of section images with the aid of multiple focus detector combinations are known, for, example, from the patent specifications U.S. Pat. No. 4,196,352, U.S. Pat. No. 4,384,359, U.S. Pat. No. 5,966,422, U.S. Pat. No. 4,991,190 and U.S. Pat. No. 6,421,412 B1. The Laid-Open Specification DE 199 57 082 A1 discloses the recording of movement signals of the heart by the use of an EKG in order to display a beating heart in parallel with the scanning process. As such, the rest phases of the heart can be determined and exclusively images from the rest phase can be assessed. The X-ray source may additionally be active only during the rest phase in the cited document.

Furthermore, reference is made to the publication T. Flohr, B. Ohnesorge, "Heart-Rate Adaptive Optimization of Spatial and Temporal Resolution for ECG-Gated Multislice Spiral CT of the Heart", JCAT vol. 25, No. 6, 2001. Algorithms for accurate-phase volume reconstruction of the heart for a cardio spiral in a multiple line CT are known from this document.

The problem of these generally known cardio spiral reconstruction methods is that the time resolution that is achieved in the scanning of a periodically moving heart is not always sufficient to achieve sufficiently sharp section image representations of the coronary vessels.

SUMMARY OF THE INVENTION

One object of an embodiment of the invention is therefore to provide a method for production of tomographic section images of periodically moving examination objects which allows better time resolution to be achieved, with the aim at the same time of using the time advantage of a multiple focus detector combination. A further aim is also to propose a CT scanner which is suitable for this purpose.

The inventors have identified that it is possible by using back-projection methods which are known per se with spiral reconstruction and reformatting to achieve better time resolution from complete 180° detector data if the detector output signals which are used from a number of detectors are combined not just from one cycle of the heart but from a number of cycles, so that the actual recording time with respect to one period of the heart is shorter, thus allowing better time resolution.

Thus, for example, when a scanning process is carried out in a CT scanner with two focus detector combinations which are offset through 90° with respect to one another on a plane, then two sinograms, which are offset through 90°, are measured at the same time.

A complete projection interval of length $\pi$ (180°) is required for a cardio reconstruction based on parallel geometry for each image layer, corresponding to the so-called 2D reconstruction method, or for each image voxel, corresponding to the so-called 3D reconstruction method. Two focus detector combinations can now be used to form one such complete 180° data record from simultaneous mutually complementary segment elements $P_1$ and $P_2$ of length $\pi/2$ (90°). An exposure time $T_{ima} = T_{rot}/4$ is thus associated with the data record and with the associated image data. In contrast, the time resolution for a single-tube system is restricted to $T_{ima} = T_{rot}/2$.

The situation described above also applies in a corresponding manner to a CT scanner with more than two foci and/or more than two X-ray tubes. It should also be mentioned that the expression an n-times focus detector combination n should be understood as relating only to the number of foci, in which case either a number of focus detector pairs with detectors whose extent covers the beam fan produced by the focus or, on the other hand, one cylindrically arranged detector of the revolving foci in each case being irradiated segment by segment. By way of example, both variants are illustrated in FIGS. 4e and 4g of Patent Specification U.S. Pat. No. 5,966,422, the entire contents of which is incorporated herein by reference.

If a 2 focus detector combination is used, which is equipped with a detector $D_1$ with a small measurement field and with a detector $D_2$ with a large measurement field, the data items which are located outside the measurement field of the detector $D_1$ and which are required for image reconstruction are supplemented from the data acquired in the detector $D_2$. The area $(-p_{1,max}, +p_{1,max})$ in this case corresponds to the extent of the small detector $D_1$, and $(-p_{2,max}, +p_{2,max})$ corresponds to the extent of the large detector $D_2$. In this case, the signal $S_1(\alpha,p,q,)$ which is measured in the first detector $D_1$ or in the detector area of the beam fan of the first focus, is used for the projection angle $\alpha$ where $\alpha_{1s} - \theta_{trans}/2 \leq \alpha \leq \alpha_{1e} + \theta_{trans}/2$ for the parallel positions in the area $-p_{1,max} \leq p \leq p_{1,max}$ in the partial angle segment $p_1$, and q denotes the q-th detector line. The signal $S2(\alpha+k\cdot 2\pi, p, \tilde{q}_k)$ which is measured in the detector $D_2$ or in the detector area of the beam fan of the second focus is entered in the area $[-p_{2,max}, -p_{1,max}[\cup]p_{1,max}, p_{2,max}]$. Since the data is measured in the spiral path with a pitch of d, and the detectors, or the corresponding detector sectors, are offset through an angle of 90°, the z position of the line $\tilde{q}$ of the second detector in the parallel geometry is given by:

$$z_2(\alpha + 2k\pi, p, \tilde{q}) = z_1(\alpha, p) - \frac{d \cdot N \cdot S}{4} + \frac{d \cdot \arcsin(p/R_f)}{2 \cdot \pi} + k \cdot d \cdot N \cdot S + (\tilde{q} - N/2) \cdot S$$

where: $R_f$ is the focus path radius, N is the number of lines and S is the collimated layer thickness.

k is now chosen to be equal to 0 if one $\tilde{q} \in \{1, \ldots, N\}$ exists, so that $z_2(\alpha,p,\tilde{q}) = z_1(\alpha,p,q)$, where $z_1(\alpha,p,q) = z_1(a,p) + (q - N/2) \cdot S$. Otherwise, k=1. Since a pitch of d~0.25 is used for cardio imaging, a choice such as this is always possible, and can thus be supplemented with signals measured in $D_2$.

The composition of the two 90° segment element sinograms $P_1$ and $P_2$ to form a complete 180° sinogram will now be described in the following text.

In this case, in order to avoid discontinuities in the transitional area of the partial angle segments, line-by-line sinogram weighting of the segment elements $P_1$, $P_2$ is required. For example, the following transitional weighting may be chosen:

$$f(\alpha) = \begin{cases} \cos^2\left(\pi/2 \cdot \frac{(\theta_{trans} - \alpha)}{\theta_{trans}}\right) & \alpha_{js} - \theta_{trans}/2 \le \alpha \le \alpha_{js} + \theta_{trans}/2; \text{ and} \\ & \alpha_{je} - \theta_{trans}/2 + \alpha \le \alpha \le \alpha_{je} + \theta_{trans}/2 \\ 1 & \alpha_{js} + \theta_{trans}/2 \le \alpha \le -\theta_{trans}/2 + \alpha_{je} \end{cases}$$

In this case, $\alpha$ denotes the projection angle and $\alpha_{js}$, $\alpha_{je} = a_{js} + \pi/2$ (j=1,2) the start and end projections of the segment elements. $\theta_{trans}$ is the length of the transitional area.

The EKG for the patient must be recorded at the same time for the continuous recording of the measurement data in the spiral mode. Measurement data can then be taken retrospectively in the correct phase from the data record and can be calculated to form CT images. In this case, a $\pi$ data area (=a data area covering a sector of 180°) is formed from a number of adjacent heart cycles in the correct phase. Instead of the $\pi$ data area, the two partial angle segments $P_1$ and $P_2$ of length $\pi/2$ occur. Each of the simultaneously measured data segments can now be formed from data in the correct phase from one or more adjacent heart cycles. In consequence, the "exposure time" for each partial angle segment is shortened further, since they are formed by subsegments with the same phase.

By way of example, the above approach will be explained in the following text for a 2-sector reconstruction in which two adjacent heart cycles contribute to the formation of the image, with the following analysis being restricted to one angle segment $P_1$. The angle segment $P_2$ can be dealt with analogously.

After the parallel rebinning process, the angle segment $P_1$ of length $\pi/2$ is measured from two adjacent heart cycles, segment elements with the correct angle and of length $\alpha_1$ and $\alpha_2$ are formed, which complement one another to form $\pi/2$. Thus, for the start angle of these segment elements in the n-th heart cycle (in this context, also see FIG. 5):

$$\alpha_{n2s} = \alpha_{n1s} + \alpha_1 + n_1 \cdot \pi/2$$

where $n_1$ is an integer and the index n denotes the number of the heart cycle under consideration.

The time positions in the EKG, $t_{n1s}$ and $t_{n2s}$, which are associated with the start angles must be separated by the same time from the corresponding R peaks. For example, these can be measured at the interval from the next R peak, that is to say:

$$t_{n1s} = T_R(k+1) - T_{rev};$$

$$t_{n2s} = T_R(k+2) - T_{rev}$$

where $T_R(k+1)$ or $T_R(k+2)$ determines the time position of the R peak of the EKG for the (k+1)-th or (k+2)-th heart cycle, respectively. $T_{rev}$ denotes the desired heart phase as the time period from the R peak.

Simple conversion operations result in the following expressions from this condition:

$$\alpha_{n2s} = \alpha_{n1s} + \alpha_1 + 2\pi \cdot \frac{T_{RR}(k+1)}{T_{rot}};$$

$$T_{RR}(k+1) = T_R(k+2) - T_R(k+1)$$

and $$\alpha_1 = \left(\frac{4T_{RR}(k+1)}{T_{rot}} - n_1\right) \cdot \pi/2;$$

$$n_1 = \left\lfloor 4 \cdot \frac{T_{RR}(k+1)}{T_{rot}} \right\rfloor; \text{ for } \alpha_1 > \pi/2$$

In this case, Trot represents the rotation time of the scanner for a 360° revolution. The time resolution in the angle segments $P_1$ and $P_2$ is determined by the maximum from $\alpha_1$ and $\alpha_2$. The time resolution of an image reconstructed from $P_1$ and $P_2$ is thus:

$$\Delta T_{ima} = \frac{T_{rot}}{4} \cdot \frac{\max(\alpha_1, \pi - \alpha_1)}{\pi/2}$$

Once the detector data has been sorted in time as described above, this results in a multiple line data record with the correct phase, which can be calculated using known 2D or 3D spiral algorithms to form image data.

In a corresponding form, the inventors propose a method for production of tomographic section images, in particular X-ray CT images, of an at least partially periodically moving examination object with periodically alternating movement and rest phases, preferably of a heart of a living being, preferably of a patient, which includes at least the following method steps:

in order to scan the examination object, n focus detector combinations—where n=2 or 3, preferably n=2—with flat detectors, at least some of which have a different extent, preferably multiple line detectors, are moved on coaxial spiral paths relative to the examination object, with detector output data which represents the attenuation of beams originating from the focus as they pass through the examination object being gathered together with indirect or direct spatial orientation data for the beams, at the same time, movement signals, preferably EKG signals, from the examination object are measured in order to detect movement and rest phases, with the time correlation between the movement data and the detector output data being stored, so that it is possible to determine retrospectively which detector data originates from which period of the movement/rest cycle, detector output signals from n detectors in individual subsegments, which together each produce a complete 180° segment and represent a rest phase of the moving object, are then combined, with the complete 180° segment being composed of n subsegments depending on the desired time resolution, and these n subsegments in turn being composed of m subsegments, preferably m=2, from m successive movement periods, and a back-projection with spiral reconstruction and reformatting being carried out with these 180° segments.

Data is thus gathered from a number of detectors and over a number of movement cycles, but over a shorter time interval in comparison to the duration of one cycle, is assembled in the correct sequence and the data items are added to one another in a complementary form to form an entire 180° data record. A data record such as this can then be calculated using the known reconstruction methods, with 2D or 3D back-projection methods, to produce tomography section images in a known manner. In this case, overall, the time resolution becomes better the greater the number of complementary focus detector combinations that are used and the greater the number of movement cycles over which the measurement is carried out. However, there are physical limits to the number of focus detector combinations and, if the number of movement cycles that are used is too great, this results in other artefacts (which result from other movement) as well as dosage problems, at least when examining patients, so that this is also subject to natural limits.

In order to simplify the subsequent computation operations for the method according to the invention, a parallel rebinning process, preferably carried out line by line, can be carried out before the back-projection.

According to one preferred variant of the method, two and only two focus detector combinations are used, whose angles are offset with respect to one another and which are preferably arranged at right angles to one another or, in another variant, three and only three focus detector combinations are used, whose angles are offset with respect to one another and which are preferably offset through 180°/3. The double combination is particularly advantageous since, in this case, at least one focus detector combination can be used very simply whose aperture angle is greater, preferably considerably greater, than the aperture angle of the at least one other focus detector combination.

In this case, the aperture angle which is used, preferably also the active area of the corresponding beam, of the larger focus detector combination can be restricted before the scanning process such that it is identical to the aperture angle or angles of the other focus detector combination or combinations.

In principle, the focus detector combinations can be arranged such that they in each case run on their own spiral path which is offset with respect to the spiral paths of the other focus detector combinations.

However, it is also possible for at least two focus detector combinations to be arranged offset with respect to one another in the z direction such that they run on a common coincident spiral path. According to an embodiment of the invention, the offset between the at least two focus detector combinations in the z direction can also be set for this purpose as a function of a chosen pitch of the spiral, so that the different pitch rates can be set, with all of the spiral paths of the focus detector combinations nevertheless remaining coincident.

In addition, it should also be mentioned that the expression a number of focus detector combinations may be understood as meaning not only an association of a number of rotating foci in pairs to form a number of co-rotating detectors, but also a system with a number of foci and a single cylindrical detector which covers 2π. In the latter variant, the data which in each case originates from the detector area which is covered by the beam of the focus under consideration should also, of course, be regarded as detector data from the respective focus detector combination.

In order to reduce the dosage load on the examination object, the radiation which originates from at least one focus can be switched off for at least the majority of the movement phase, controlled indirectly or directly by the measured movement signals.

One particular embodiment of the method according to an embodiment of the invention may include the data from the focus detector combination with a small fan angle, which covers a relatively small section field, being used by data from the focus detector combination with a large fan angle, which covers a larger section field, to supplement the detector data from the larger detector.

In order to improve the image quality and in order to avoid artifacts at the junctions between the data from different detectors and different cycles, it is advantageous, during the combination of the data records from different detectors, for a transitional weighting to be produced between the data records, preferably between segment elements from the data records.

In particular, the data records from each focus detector combination, preferably the segment elements of the data records, may also be subjected to sinogram weighting in order to prevent image artifacts.

In a corresponding way to the method according to an embodiment of the invention, the inventors also propose an imaging CT scanner, in particular an X-ray CT scanner, which has at least the following features:

two coaxially arranged focus detector combinations which can be moved in a spiral shape along a common rotation axis in order to scan a periodically moving object, a means for movement detection and in order to distinguish between rest and movement phases of the periodically moving object, preferably an EKG, and means for storage and processing of detector output data by means of 2D or 3D spiral reconstruction relating to tomography section images, with means, preferably program means, being provided and being designed such that the method steps described above are carried out during operation.

A CT scanner such as this may have at least two focus detector combinations with fan aperture angles $\beta_1$, $\beta_2$ of different size, in which case the size of the fan aperture angle $\beta$ on at least one focus detector combination is designed to be adjustable.

Furthermore, the distance between the focus and the detector may be different for two focus detector combinations.

BRIEF DESCRIPTION OF THE DRAWINGS

The invention will be explained in more detail in the following text with reference to a preferred exemplary embodiment and with the aid of figures, in which the following reference symbols and variables are used: 1 CT scanner; 2 first tube; 3 first detector; 4 second tube; 5 second detector; 6 housing; 7 opening; 8 couch; 9 system axis/z axis; 10 control/evaluation unit; 11 first beam; 12 second beam; 13 first/small section field; 14 second/large section field; 15 shutter for the second beam; 16 shutter for the first beam; 17 R peak in the EKG; 18 EKG line; 19 reconstructable volume element with data from one heart cycle; 20 reconstructable volume element with data from two heart cycles; 21 time back to the start of the rest phase; 22 detector lines; 23 virtual detector; $D_1$ first detector; $D_2$ second detector; d pitch; k the number of the half revolution of the gantry; $L_1$ length of the first detector; $L_2$ length of the second detector; P patient; p parallel positions on a parallel projection; $Prg_n$ n-th program module; $P_n$ π/2 partial data record; $P_{n,max}$ maximum position of the detector n; q number of lines; $R_f$ focus path radius; S layer thickness; $S_n$ n-th spiral data record; $T_{rev}$ time delay with respect to the R peak; $T_R$ time of the R peak; $T_{RR}$ duration of one heart cycle from one R peak to the next; $T_{rot}$ revolution time of the gantry; z z axis; $z_n$ z position of the n-th detector; $z_{img}$ z position of the image; α rotation angle of the gantry/projection angle; $α_n$ start angle; $α_{js}$ start projections of the segment elements; $α_{je}$ final projections of the segment elements; $α_{nms}$ m-th start angle of the n-th focus; $β_1$ fan angle of the first beam; $β_2$ fan angle of the second beam; $Δt_{ima}$ time image resolution; $Θ_n$ n-th segment element; $Θ_{trans}$ length of the transition area.

In detail, in the figures.

DETAILED DESCRIPTION OF THE EXEMPLARY EMBODIMENTS

Figure 1:
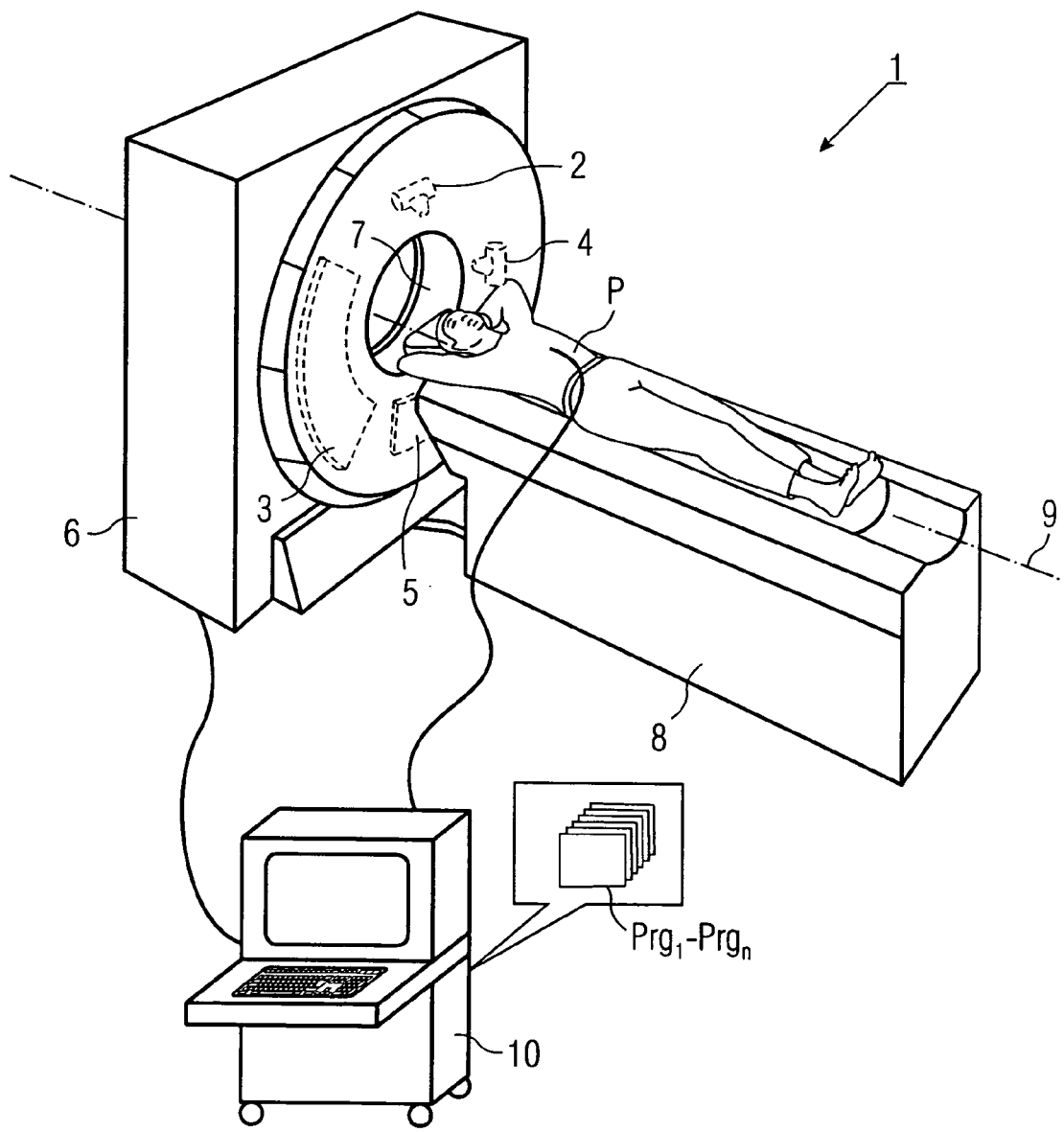
FIG. 1: shows a 3D illustration of a CT scanner with two focus detector combinations including an evaluation unit.

FIG. 1 shows a 3D illustration of one preferred exemplary embodiment of a CT scanner 1 with two focus detector combinations 2, 3 and 4, 5, which can be rotated within the housing 6 on a gantry, which is not illustrated. However, the illustration shows only X-ray tubes 2 and 4, since the actual focus is located within the tubes. Controlled by the control and evaluation unit 10, the patient P is moved along the z axis 9 with the aid of the movable patient couch 8 through the opening 7 in the CT scanner 1 while, at the same time, the gantry rotates with the two focus detector combinations 2, 3 and 4, 5 about the z axis 9. With respect to the patient as the reference system, this results in spiral movement paths of the focus detector combinations. If the focus detector combinations are arranged on one plane, then each focus detector combination runs on its own spiral path, which is shifted with respect to the other spiral path corresponding to its angle offset.

At the same time as the scanning of the patient P with the focus detector combinations, the movement signals of the heart are scanned by means of an EKG which is integrated in the control/evaluation unit 10, from which it is possible to retrospectively determine the previous rest phase in time with respect to the currently measured heart cycle, on the basis of the R peak detected in the EKG.

Figure 2:
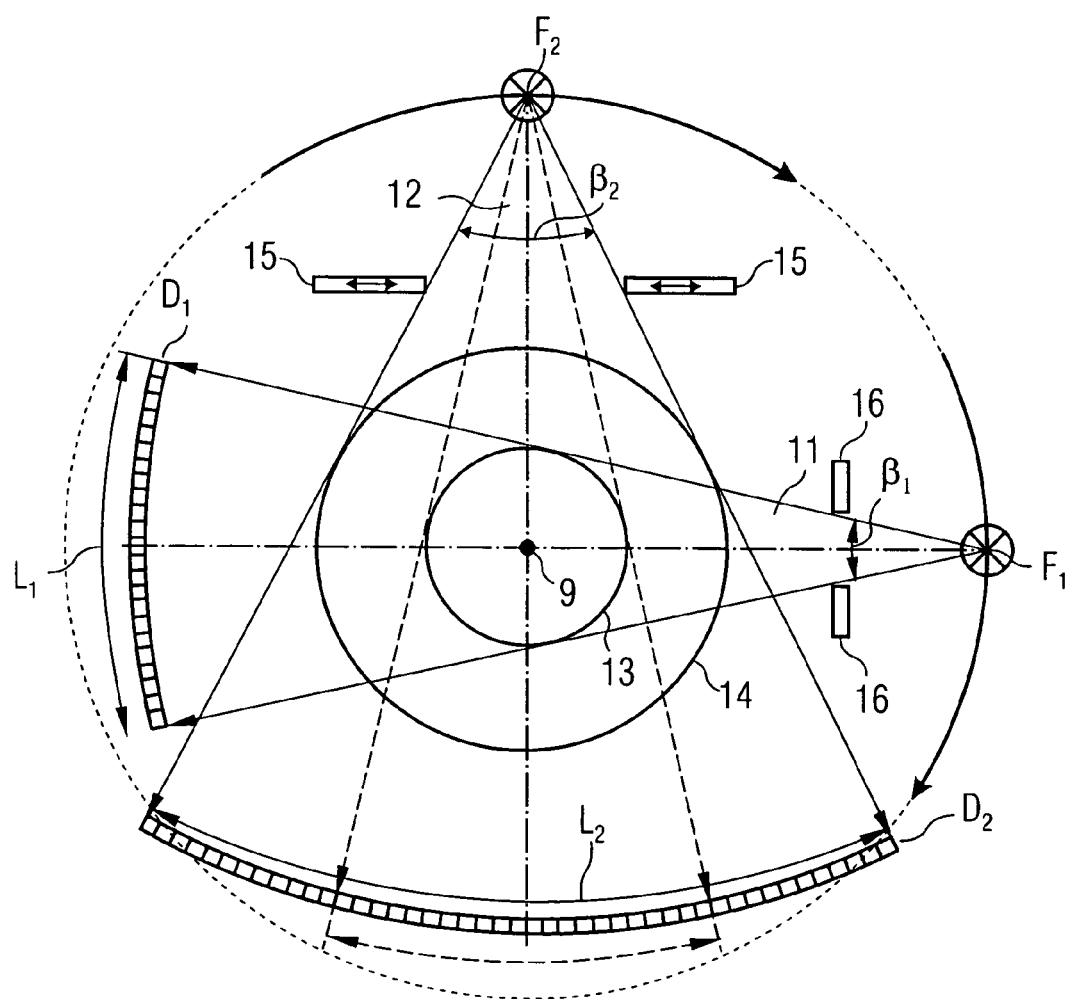
FIG. 2: shows a schematic illustration of a recording system with two focus detector combinations, respectively having a large and a small fan angle, in each case offset through 90° with respect to one another.

In order to assist understanding, FIG. 2 shows the scanning system of the two focus detector combinations once again in the form of a schematic section illustration, although the X-ray tubes forming the respective foci $F_1$ and $F_2$ are not illustrated here. This illustration thus shows the two focus detector combinations from FIG. 1, respectively with a first focus $F_1$ and a second focus $F_2$, and the respective multiple line detectors $D_1$ and $D_2$ arranged opposite them. A beam 11 with a smaller fan angle $β_1$, which is set in a fixed manner by the shutter 16, extends from the focus $F_1$ to the opposite detector $D_1$, which has a length $L_1$ in the direction of the fan angle $β_1$ and has a number of detector lines in the z direction.

The second focus detector combination $F_2$, $D_2$ is arranged essentially at right angles to the X-ray beam center line from the focus $F_1$ to the detector $D_1$. These focus detector combinations $F_2$, $D_2$ have a variable, larger fan angle $β_2$, however, whose aperture angle can be set on the one hand to the angle of the first beam fan $β_1$ or to a broader angle. The fan angle is in this case set by means of a movable shutter 15. If, exceptionally, both fan angles are set to be of the same magnitude, then only the area located in the small section field 13 is scanned, while the wider section field 14 can be scanned completely if the beam 12 is set to be wider.

If the beams are set to have different widths, then data from the smaller section field 13 from the smaller detector $D_1$ can have data from the larger section field 14 from the larger detector $D_2$ added to it. This principle of supplementing data is described in more detail in FIG. 3. If the two beams are set to be the same, then no addition by the second focus detector combination is possible in the area beyond the smaller section field 13. The length of the second detector $L_2$ is also designed to correspond to the adjustable maximum width of the fan angle $β_2$, in which case only a central part of the detector may possibly be active.

Figure 3:
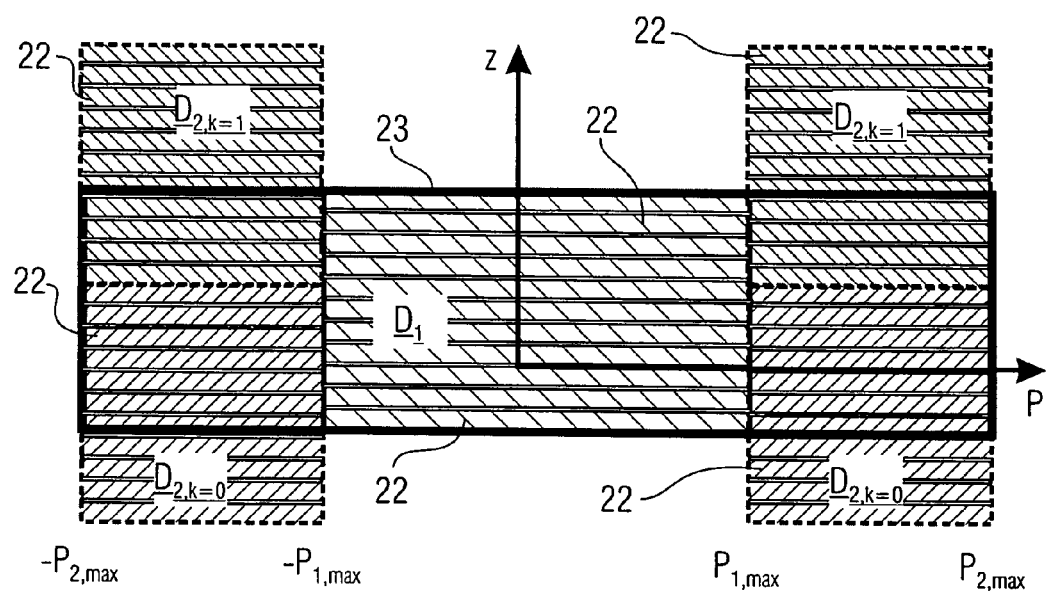
FIG. 3: shows a schematic illustration of the line-by-line progress of the data from two detectors.

FIG. 3 shows the principle of line-by-line supplementing or line-by-line continuation of the data from the first smaller detector $D_1$ in the area $[-P_{2,max},-P_{1,max}[∪]P_{1,max},P_{2,max}]$ with data, which is at the correct angle but precedes it by π/2 in the spiral path, from the larger detector $D_2$, in the projection angle α with respect to the parallel geometry. The additional indices k=0 and k=1 for the detectors $D_{n,k}$ denote the instantaneous and the subsequent half revolution in the spiral path. The virtual detector 23, which is projected to the center of rotation, is illustrated highly schematically, in fact, the detector lines 22 at the center of rotation have convex curvature in the parallel geometry, and are inclined in a corresponding manner to the spiral path.

Figure 4:
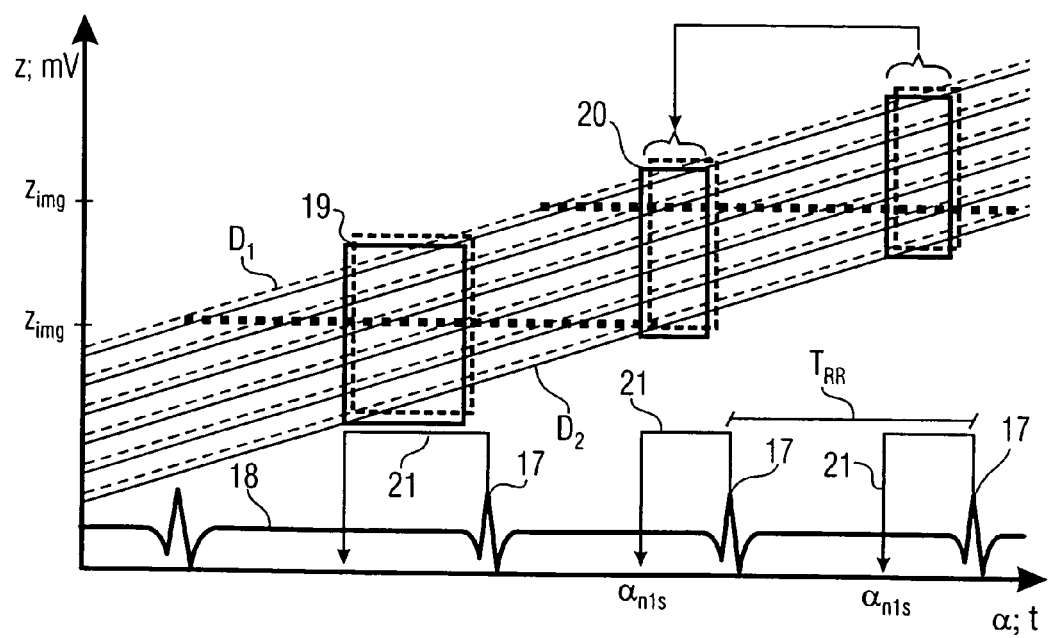
FIG. 4: shows the position profile of two detectors in the z direction as a function of the rotation angle of the gantry in the spiral mode with an EKG signal in order to illustrate 2-sector reconstruction of an image position.
Figure 5:
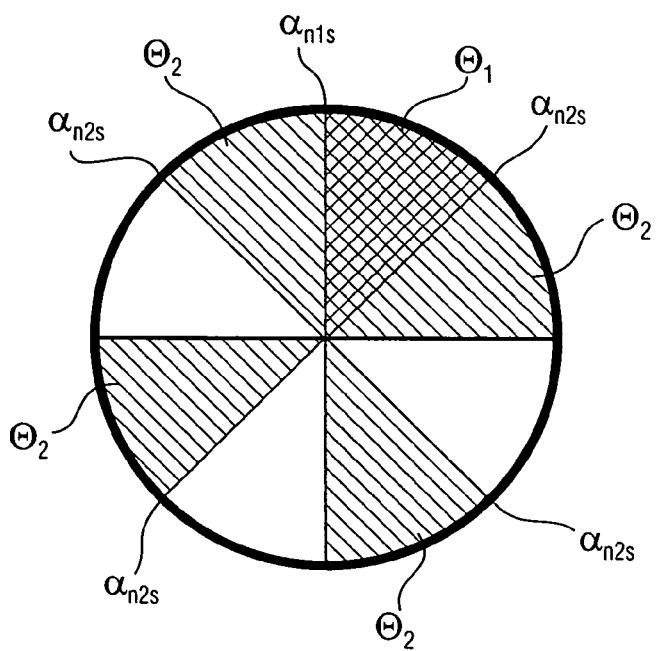
FIG. 5: shows the principle of sector selection for a 2-sector reconstruction.

The algorithm for 2-sector reconstruction, which has been developed for reconstruction of spiral data from two focus detector combinations, is described in FIGS. 4 and 5 with reference to the preferred exemplary embodiment with two foci.

FIG. 4 shows, schematically, the profile of the detectors plotted against the z axis in relation to the rotation angle α, which is linearly coupled to the time axis t, since the spiral profile is constant. The profile of the EKG line 18—mV/t coordinate—is shown directly related at the bottom, plotted against the time with the R peaks 17. The start of the rest phase in each heart cycle is determined retrospectively from the position of the R peak, illustrated by the reference symbol 21. The spiral data records $S_1$ and $S_2$ recorded in the spiral mode with the two detectors $D_1$ and $D_2$ are used for display purposes from this time in the cycle. The lines which run obliquely from the bottom left represent the path of the detector lines along the z axis, with the dashed lines representing the profile of the detector lines of the detector $D_1$, and the solid lines representing the profile of the detector $D_2$.

With regard to the first reconstructable volume element of the heart, this shows a reconstruction from data 19 from a single heart cycle, while the data in the area of the curly brackets 20 from two successive heart cycles is used for the subsequent reconstruction, with this data being combined for an image position $z_{img}$. This results in better time resolution and thus in a sharper display of the heart and, in particular, of the coronaries. This can be seen in the illustration by the reduced time extent of the data gathered at 20.

After line-by-line resorting of the fan data to form parallel data, parallelized data records are obtained in the first reconstruction step once the rebinning process has been carried out.

A projection interval of length $\pi$ is required for each image layer for a cardio reconstruction using parallel geometry. Using a 2-focus detector system, a data record such as this can be formed from simultaneous, mutually complementary, segment elements of length $\pi/2$ from the spiral data records $S_1$ and $S_2$. The detector $D_1$ has only a restricted measurement field for CT heart imaging. Reconstructions can also be produced in a larger image window than the actually known representation of the section field, which is restricted corresponding to the fan angle, from data from the first detector $D_1$ which has data from the second detector $D_2$ added to it with the correct angle. This corresponds to the second reconstruction step.

After parallel sorting and after data supplementing as described above, a one-dimensional parallel projection is determined from the parallel conical beam projections on a projection basis from each of the two spiral data records $S_1$ and $S_2$, by way of spiral interpolation, for a predetermined image position $z_{img}$. In this case, the z distance between the beams and the image position $z_{img}$ under consideration is weighted on a channel basis. In this case, as is shown in FIG. 4, only projections from $S_1$ or $S_2$ which have been acquired with the correct phase are considered, and are added to one another with the correct angle to form $\pi/2$. This corresponds to the reconstruction step 3 in the reconstruction pipeline.

With regard to spiral interpolation, which is known per se, reference should be made to the literature reference T. Flohr, B. Ohnesorge, "Heart-Rate Adaptive Optimization of Spatial and Temporal Resolution for ECG-Gated Multislice Spiral CT of the Heart", JCAT vol. 25, No. 6, 2001, whose entire disclosure content is incorporated herein by reference.

FIG. 5 shows the principle of acquisition of the two spiral data records $S_1$ and $S_2$ in the correct phase. Corresponding to the ratio of four times the interval between the two R peaks in the EKG to the duration of one complete revolution of the gantry $4T_{RR}/T_{rot}$, which corresponds to a first spiral data record $S_1$, which corresponds to a first sector $\Theta_1$ which starts at the rotation angle $\alpha_{n1s}$ of the gantry, the second sector $\Theta_2$, which is in each case added to form $\theta/2$, can likewise be selected from the spiral data record $S_1$. The spiral data record $S_2$ is now dealt with analogously to this rule.

Here, by way of example, a first sector $\Theta_1$ is shown, to which in principle any desired other illustrated sectors $\Theta_2$ can be added to form an overall sector covering $\pi/2$, with these being not only the two directly adjacent sectors but also their complementary sectors offset through $\pi$, which contain the same information. The illustrated first sector $\Theta_1$ can thus have four other sectors $\Theta_2$ added to it. Which of the four angle positions of $\Theta_2$ is actually used in the respective situation at any given time depends on the ratio of the rotation time to the heart cycle length $(T_{rot}/T_{RR})$.

According to an embodiment of the invention, in order to achieve better time resolution than the known single-sector reconstruction in the two-sector reconstruction described here, data from adjacent heart cycles is used for image construction, thus resulting in a 180° data record comprising in each case two sectors with in each case two subsegments. The two subsegments of length $\Delta\Theta_1$, $\Delta\Theta_2=\pi/2-\Delta\Theta_1$ have respective start and end projections $\alpha_{n1s}$, $\alpha_{n1e}$ and $\alpha_{n2s}$ and $\alpha_{n1e}$ (corresponding to the time positions $t_{n1s}$, $t_{n1e}$ as well as $t_{n2s}$ and $t_{n2e}$). The requirement for segment elements with the correct angle means that:

$$\alpha_{2ns}=\alpha_{1ns}+\Delta\Theta_1+n1\cdot\pi/2$$

where $n_1$ is a natural number that has not yet been determined.

Furthermore, the projections must be in the correct phase, that is to say $t_{n1s}$ and $t_{n2s}$ must be separated by the same time from the corresponding R peaks in the EKG. For example: $t_{n1s}=T_R(n+1)-T_{rev}$ and $t_{n2s}=T_R(n+2)-T_{rev}$; where $T_{rev}$ denotes a time offset before the subsequent R peak. The same time interval means:

$$\alpha_{2ns} = \alpha_{1ns} + 2\pi \frac{T_{RR}(n+1)}{T_{rot}} - n_1 \cdot \pi/2$$

where $T_{RR}(n+1)=T_R(n+2)-T_R(n+1)$ denotes the current heart cycle length and $T_{rot}$ denotes the rotation time of the gantry. Simple conversions result in:

$$\Delta\Theta_1 = \left(\frac{4T_{RR}}{T_{rot}} - n_1\right)\cdot\pi/2$$

$$n_1 = \left[\frac{4T_{RR}}{T_{rot}}\right]$$

The four possible situations of complementary supplementing of $\Delta\Theta_1$ and $\Delta\Theta_2$ sketched in FIG. 5 result depending on the current heart frequency and the gantry rotation time $T_{rot}$. For $\Delta\Theta_2$, $\Delta\Theta_2=\pi/2-\Delta\Theta_1$. Two single-line $\pi/2$ data record elements $P_1$ and $P_2$ are then produced after the spiral interpolation of the spiral data records $S_1$ and $S_2$ (which have been sorted with the correct phase) of time-sorted data.

In order to average data inconsistencies on segment transitions, transitional weighting of the sectors as well as transitional weighting of $P_1$ and $P_2$ may then be required both within the $\pi/2$ data record elements $P_1$ and $P_2$, respectively. The subsequent transitional weighting process is normally carried out by using $\sin^2$ weights, a so-called sinogram weighting, in the respective transitional area between the sectors, and corresponds to the fourth reconstruction step.

The following text describes image calculation by way of the filtered 2D back-projection, which is known per se, and as generally known. By way of example, reference should in this context be made to DE 10 207 623 A1, the entire contents of which are hereby incorporated herein by reference, with further references. Alternatively, however, it is also possible to use a 3D back-projection method, which is generally known per se, and is disclosed, by way of example, in DE 10 159 927 A1, the entire contents of which are hereby incorporated herein by reference.

Thus, overall, this results in the following reconstruction pipeline:
1. Line-by-line parallel rebinning;
2. Line-by-line continuation of the spiral data records from $S_1$ in the channel direction with data from $S_2$;
3. Spiral interpolation of the spiral data records $S_1$ and $S_2$ of time-sorted data to form single-line $\pi/2$ data record elements $P_1$ and $P_2$;

4. Transitional weighting of the π/2 data record elements $P_1$ and $P_2$ with final sinogram weighting;
5. Filtered 2D or 3D back-projection of the single-line π data record.

Since the spiral data records $S_1$ and $S_2$ are acquired at the same time, this results in an associated time resolution $\Delta T_{ima}=T_{rot}/4$ for the segment elements $P_1$ and $P_2$ in a known single-sector reconstruction. Thus, with the gantry rotation time $T_{rot}$ of about 400 ms which is possible at the moment, this results in a time resolution of about 100 ms, which is comparable to EBT, even with a single-sector reconstruction. In the case of the two-sector reconstruction according to the invention, the time resolution depends on the heart rate and is defined by $$\Delta T_{ima} = \frac{\max(\Delta \Theta_1, \Delta \Theta_2)}{2\pi} T_{rot}.$$

In a good situation, this thus results in $\Delta T_{ima}=T_{rot}/8$, while in a poor situation, where $\Delta \Theta_1=\pi/2$, the time resolution becomes $\Delta T_{ima}=T_{rot}/4$.

Figure 6:
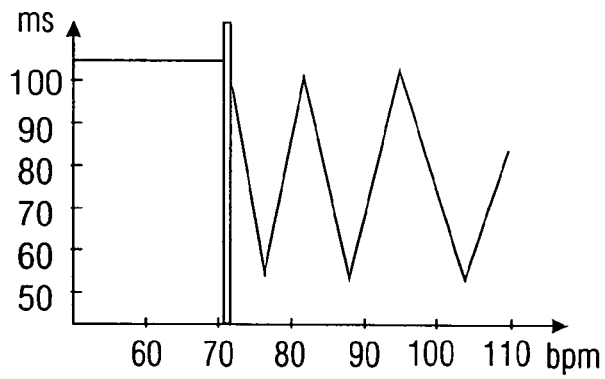
FIG. 6: shows the time resolution of the image data as a function of the heart rate for a 2-tube arrangement with a rotation time $T_{Rot}$ of 420 ms.
Figure 7:
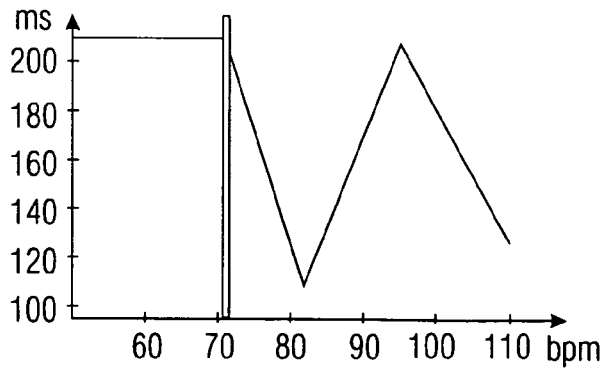
FIG. 7: shows the time resolution of the image data as a function of the heart rate for a single-tube arrangement with a rotation time $T_{Rot}$ of 420 ms.

According to one special embodiment of the method, it is possible to design the time sorting to be carried out adaptively, that is to say the single-sector reconstruction is used for lower heart rates, while the two-sector reconstruction is used for higher heart rates. FIGS. 6 and 7 show the time resolution as a function of the heart rate. For a CT scanner with a single-focus detector combination with the same rotation time, the result is illustrated in FIG. 6, while the result for a CT scanner with two focus detector combinations is illustrated in FIG. 7. The theoretical values for $\Delta T_{ima}$ are, however, dependent on the parallel rebinning process and the transitional or sinogram weighting not being achieved exactly.

In this case, it should be noted that the spiral pitch should be limited such that the volume elements which are reconstructed in each heart cycle are adjacent to one another without any gaps, as is described in the literature reference T. Flohr, B. Ohnesorge, "Heart-Rate Adaptive Optimization of Spatial and Temporal Resolution for ECG-Gated Multi-slice Spiral CT of the Heart", JCAT vol. 25, No. 6, 2001, the entire contents of which are hereby incorporated herein by reference.

It should be noted that the statements made above can also be applied in a generalized form to more than two focus detector combinations, with appropriate adaptation of the computation principles being required corresponding to the number of foci. However, the use of two focus detector combinations appears to be particularly advantageous.

Thus, overall, an embodiment of this invention discloses a method which uses a combination of detector data, added in the correct phase, to significantly improve the time resolution of a CT scanner, on the one hand based on a number of focus detector combinations which scan an examination object at the same time, and on the other hand based on a number of adjacent movement cycles of a periodically moving examination object, with the reconstruction of the CT images in each case being carried out using π data records which have been joined together completely in advance.

It is self-evident that the features of the invention which have been mentioned above may be used not only in the respectively stated combination but also in other combinations or on their own without departing from the scope of the invention.

What is claimed is:

1. A method for production of tomographic section images of an at least partially periodically moving examination object with periodically alternating movement and rest phases, comprising:
    moving, to scan the examination object, n focus detector combinations, wherein n is at least one of 2 and 3, on coaxial spiral paths relative to the examination object, with detector output data representing attenuation of beams passing through the examination object being gathered together with at least one of indirect and direct spatial orientation data for the beams;
    measuring movement signals from the examination object to detect movement and rest phases;
    storing a time correlation between the movement data and the detector output data so that it is possible to determine retrospectively which detector data originates from which period of the movement/rest cycle;
    combining detector output signals from n detectors in individual subsegments, which together each produce a complete 180° segment and represent a rest phase of the moving object, wherein the complete 180° segment is composed of n subsegments depending on the desired time resolution, and wherein the n subsegments are composed of m subsegments from m successive movement periods; and
    carrying out a back-projection with spiral reconstruction and reformatting with the 180° segments.

2. The method as claimed in claim 1, wherein a parallel rebinning process is carried out before the back-projection.

3. The method as claimed in the claim 2, wherein the parallel rebinning process is carried out line by line.

4. The method as claimed in claim 3, wherein a 2D back-projection is carried out as the back-projection method.

5. The method as claimed in claim 3, wherein a 3D back-projection is carried out as the back-projection method.

6. The method as claimed in claim 2, wherein a 2D back-projection is carried out as the back-projection method.

7. The method as claimed in claim 2, wherein a 3D back-projection is carried out as the back-projection method.

8. The method as claimed in claim 1, wherein a 2D back-projection is carried out as the back-projection method.

9. The method as claimed in claim 1, wherein a 3D back-projection is carried out as the back-projection method.

10. The method as claimed in claim 1, wherein two and only two focus detector combinations are used, whose angles are offset with respect to one another.

11. The method as claimed in claim 10, wherein the two focus detector combinations are arranged at right angles to one another.

12. The method as claimed in claim 1, wherein three and only three focus detector combinations are used, whose angles are offset with respect to one another.

13. The method as claimed in claim 12, wherein the data from the focus detector combination with a small fan angle, which covers a relatively small section field, is used along with data from the focus detector combination with a large fan angle, which covers a larger section field, to supplement the detector data from the larger detector combination with the small fan angle.

14. The method as claimed in claim 12, wherein the three focus detector combinations are offset through 180°/3.

15. The method as claimed in claim 1, wherein at least one focus detector combination is used, whose aperture angle $\beta_2$ is greater than the aperture angle $\beta_1$ of the at least one other focus detector combination.

16. The method as claimed in claim 1, wherein each focus detector combination runs on its own spiral path which is offset with respect to the spiral paths of the other focus detector combinations.

17. The method as claimed in claim 1, wherein at least two focus detector combinations are arranged offset with respect to one another in the z direction such that they run on a common coincident spiral path.

18. The method as claimed in claim 17, wherein the offset between the at least two focus detector combinations in the z direction is set as a function of a chosen pitch of the spiral.

19. The method as claimed in claim 1, wherein, in order to reduce the dosage load on the examination object, the radiation which originates from at least one focus is controlled at least one of indirectly and directly by the measured movement signals being switched off over at least the majority of the movement phase.

20. The method as claimed in claim 1, wherein, during the combination of the data records from different detectors, a transitional weighting is produced between the data records.

21. The method as claimed in claim 20, wherein a transitional weighting is produced between segment elements from the data records.

22. The method as claimed in claim 1, wherein, in order to prevent image artifacts, data records from each focus detector combination, are subjected to sinogram weighting.

23. The method of claim 1, wherein the method is for production of X-ray CT images, and wherein the at least partially periodically moving examination object is a heart of a living being.

24. The method of claim 1, wherein the n focus detector combinations are 2.

25. The method as claimed in claim 1, wherein, in order to prevent image artifacts, data records from the segment elements of the data records, are subjected to sinogram weighting.

26. An imaging CT scanner, comprising:
two coaxially arranged focus detector combinations, movable in a spiral shape along a common rotation axis to scan a periodically moving object;
means for movement detection and for distinguishing between rest and movement phases of the periodically moving object;
means for storage and processing of detector output data by at least one of 2D and 3D spiral reconstruction relating to tomography section images; and
means for performing the method steps as claimed in claim 1.

27. A CT scanner as claimed in claim 26, wherein at least two focus detector combinations use fan aperture angles of different size.

28. The CT scanner as claimed in claim 27, wherein the size of the fan aperture angle on at least one focus detector combination is designed to be adjustable.

29. The CT scanner as claimed in claim 28, wherein the distance between the focus and the detector is different for two focus detector combinations.

30. The CT scanner as claimed in claim 27, wherein the distance between the focus and the detector is different for two focus detector combinations.

31. The CT scanner as claimed in claim 26, wherein the distance between the focus and the detector is different for two focus detector combinations.

* * * * *